United States Patent [19]

Newton

[11] Patent Number: 5,591,695
[45] Date of Patent: Jan. 7, 1997

[54] HERBICIDAL [1,3,4]OXADIAZOLES AND THIADIAZOLES

[75] Inventor: Trevor W. Newton, Schwabenheim, Germany

[73] Assignee: American Cyanamid Co., Madison, N.J.

[21] Appl. No.: 449,046

[22] Filed: May 24, 1995

[30] Foreign Application Priority Data

Feb. 8, 1995 [EP] European Pat. Off. .............. 95101695

[51] Int. Cl.$^6$ .................... C07D 271/10; C07D 285/12; A01N 43/824
[52] U.S. Cl. .................... 504/263; 504/265; 548/136; 548/138; 548/143
[58] Field of Search .................... 548/136, 138, 548/143; 504/263, 265

[56] References Cited

U.S. PATENT DOCUMENTS

| | | | |
|---|---|---|---|
| 3,790,588 | 2/1974 | Dahle | 548/136 |
| 4,256,632 | 3/1981 | Wolf et al. | 548/136 |
| 4,797,148 | 10/1989 | Hagen et al. | 548/136 |
| 5,294,596 | 3/1994 | Haas et al. | 548/136 |

FOREIGN PATENT DOCUMENTS

| | | |
|---|---|---|
| 2853196 | 6/1980 | Germany . |
| 229408 | 11/1985 | Germany . |
| 9313083 | 7/1993 | WIPO . |

OTHER PUBLICATIONS

March, Advanced Organic Chemstry 4th Ed. p. 1275 (1992).
Potts, Comprehensive heterocyclic Chemistry, vol. 6, p. 444 (1984).
D. Moderhack, Chem. Ber. 108, 887–896 (1975).
R. M. Paton., et al., J. Chem. Soc., Perkin Trans., 1517 (1985).

Primary Examiner—Robert Gerstl
Attorney, Agent, or Firm—John W. Hogan, Jr.

[57] ABSTRACT

Novel herbicidal compounds of the general formula I

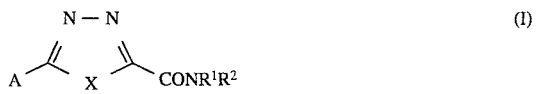

wherein X represents an oxygen or sulphur atom; A represents an optionally substituted alkyl, alkenyl, cycloalkyl, cycloalkenyl, dialkylamino, aryl, heteroaryl, aralkyl or heteroalkyl group; $R^1$ represents a hydrogen atom, an optionally substituted alkyl group or an optionally substituted acyl group; and $R^2$ represents an optionally substituted aralkyl or heteroaralkyl group; together with their preparation, formulation and use.

9 Claims, No Drawings

HERBICIDAL [1,3,4]OXADIAZOLES AND THIADIAZOLES

This invention relates to certain novel N-aralkyl and N-heteroaralkyl amides of [1,3,4]-oxadiazole- and [1,3,4]-thiadiazole-carboxylic acids, to the preparation of such compounds, to herbicidal compositions containing such compounds, and to a method of combating undesired plant growth using such compounds.

Amides of [1,3,4]oxadiazole- and [1,3,4]thiadiazole-carboxylic acids are well known. Some of these compounds have been reported to have useful properties; for example, DD 229,408 discloses a method for the preparation of certain [1,3,4]thiadiazole-carboxamides and proposes their use as biocides or intermediates therefor without disclosing their biological activity.

Amides of some [1,3,4]oxadiazole-carboxylic acids have also been claimed to have herbicidal activity; for instance, EP 224,823 and EP 581,133 disclose amides of [1,3,4] oxadiazole-substituted quinoline derivatives and triazolin-5-ones, respectively, both of which are claimed to be herbicidally active. Additionally, EP 569,810 discloses herbicidal sulfonylated amides of a variety of heterocycles, including [1,3,4]oxadiazoles.

U.S. Pat. No. 3,790,588 discloses aryl [1,3,4]oxa- and [1,3,4]thiadiazole-dialkylamines and their use as herbicides. However, their activity in terms of dosage, spectrum and selectivity is not satisfactory.

We have now found that, surprisingly, a novel class of [1,3,4]oxadiazole- and [1,3,4]thiadiazole-carboxamides in which the amide bears an N-aralkyl or an N-heteroaralkyl group, exhibits excellent herbicidal activity.

Accordingly, the present invention provides novel compounds of the general formula

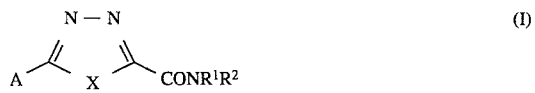

(I)

wherein X represents an oxygen or sulphur atom; A represents an optionally substituted alkyl, alkenyl, cycloalkyl, cycloalkenyl, dialkylamino, aryl, heteroaryl, aralkyl or heteroaralkyl group; $R^1$ represents a hydrogen atom, an optionally substituted alkyl group or an optionally substituted acyl group; and $R^2$ represents an optionally substituted aralkyl or heteroaralkyl group.

Generally, when any of the above mentioned moieties comprises an alkyl group this alkyl group may be linear or branched and may suitably contain 1 to 10, preferably 1 to 6 carbon atoms. Examples of such groups are methyl, ethyl, n-propyl, i-propyl, n-butyl, i-butyl, s-butyl, t-butyl, n-pentyl, i-pentyl, s-pentyl and neopentyl groups. An alkenyl group may suitably contain 2 to 8 carbon atoms. A cycloalkyl or cycloalkenyl group may have from 3 to 8 carbon atoms, most preferably 3 to 6 carbon atoms, and especially 5 or 6. An acyl group consists of a carbonyl group connected to an optionally substituted alkyl, aryl or heteroaryl group and suitably contains from 2 to 8 carbon atoms.

An aralkyl group consists of an alkyl group, defined as above, substituted by an aryl group. An aryl group is suitably an optionally substituted phenyl or naphthyl group. A heteroaralkyl group consists of an alkyl group, defined as above, substituted by a heteroaryl group. A heteroaryl group may be mono- or polycyclic. It suitably comprises 5- and/or 6-membered heterocycles, containing one or more sulphur and/or nitrogen and/or oxygen atoms. Any or all of the constituent groups may be optionally substituted.

When any groups are designated as being optionally substituted, the substituent groups which are optionally present may be any of those customarily employed in the development of pesticidal compounds, and/or the modification of such compounds to influence their structure/activity, persistence, penetration or other property. In relation to moieties defined above as comprising an optionally substituted alkyl, alkenyl or cycloalkyl group, including alkyl parts of aralkyl, heteroaralkyl or acyl groups, specific examples of such substituents include halogen, especially fluorine, chlorine or bromine atoms, and phenyl, nitro, cyano, hydroxyl, $C_{1-4}$ alkoxy, $C_{1-4}$ alkyl, $C_{1-4}$ haloalkoxy, ($C_{1-4}$ alkoxy)carbonyl groups, amino, alkyl- and phenylsulphinyl, -sulphenyl and -sulphonyl groups, and mono- or di-($C_{1-4}$ alkyl)amino groups. It is preferred, however, that such moieties are unsubstituted, or halogen-substituted.

In relation to moieties defined above as comprising an optionally substituted aryl or heteroaryl group, including aryl and heteroaryl parts of aralkyl, heteroaralkyl and acyl groups, optional substituents include halogen, especially fluorine, chlorine and bromine atoms, and nitro, cyano, amino, hydroxyl, $C_{1-4}$ alkyl, $C_{1-4}$ haloalkyl (especially $CF_3$), $C_{1-4}$ alkoxy and $C_{1-4}$ haloalkoxy groups. 1 to 5 substituents may suitably be employed.

The compounds according to general formula I are oils, gums, or, predominantly, crystalline solid materials. They are superior through their valuable herbicidal properties. For example, they can be used in agriculture or related fields for the control of undesired plants. The compounds of general formula I according to the invention possess a high herbicidal activity within a wide concentration range and may be used in agriculture without any difficulties.

Preferably, A represents an optionally substituted alkyl, cycloalkyl, alkenyl, dialkylamino, phenyl, pyridyl, furyl or thienyl group.

Especially preferred are those embodiments wherein A represents a branched $C_{3-6}$ alkyl group, a cyclopentyl group, a styryl group, a dimethylamino group, or a phenyl group which is unsubstituted, or substituted by one or two moieties independently selected from halogen atoms, $C_{1-4}$ alkyl groups, $C_{1-4}$ alkoxy groups and $C_{1-4}$ haloalkyl groups.

Preferably, X represents an oxygen atom.

Preferably $R^1$ represents a hydrogen atom.

A preferred optionally substituted aralkyl or heteroaralkyl group $R^2$ is either a phenylalkylene, in which the phenyl moiety is optionally substituted by 1 or 2 moieties independently selected from halogen and $C_{1-4}$ alkyl, or a heteroarylalkylene, in which the heteroaryl moiety is a furyl, pyridyl, thienyl or benzothiophene group, the alkylene moiety in either case being a methylene group or a $C_{2-4}$ alkylene group, which is straight chained or branched.

In general, preferred groups $R^2$ conform to the general formula

—CH($R^3$)$R^4$ wherein $R^3$ represents a hydrogen atom or an optionally substituted $C_{1-2}$ alkyl group, and $R^4$ represents an optionally substituted phenyl group, or an optionally substituted pyridyl, furyl, thiophenyl or benzothiophene group.

Preferably, $R^3$ represents a hydrogen atom or a methyl group and $R^4$ represents an unsubstituted phenyl group or thiophenyl group.

Included in the scope of the present invention are all possible enantiomers and diastereoisomers of general formula I having one or more optical centres, and also salts, N-oxides and acid addition compounds.

Particularly interesting activity has been found in (S)-isomer compounds of general formula I, wherein $R^2$ represents the group —CH($R^3$)$R^4$, of which the C atom is the stereogenic center.

The invention is exemplified by the following specific compounds:

(R/S)-5-Phenyl-[1,3,4]oxadiazole-2-carboxylic acid, [1-(2-thienyl)ethyl]amide;
(S)-5-tert-Butyl-[1,3,4]oxadiazole-2-carboxylic acid, [1-(2-thienyl)ethyl]amide;
(S)-5-Phenyl-[1,3,4]oxadiazole-2-carboxylic acid, (1-phenylethyl) amide;
(R/S)-5-tert-Butyl-[1,3,4]oxadiazole-2-carboxylic acid, [1-(2-thienyl)ethyl]amide;
(R/S)-5-(4-Fluorophenyl)-[1,3,4]oxadiazole-2-carboxylic acid, (1-phenylethyl) amide;
(S)-5-(2-Fluorophenyl)-[1,3,4]oxadiazole-2-carboxylic acid, (1-phenylethyl)amide;
(S)-5-(4-Chlorophenyl)-[1,3,4]oxadiazole-2-carboxylic acid, (1-phenylethyl)amide;
5-(4-tert-Butylphenyl)-[1,3,4]oxadiazole-2-carboxylic acid, (2-thienylmethyl)amide;
(S)-5-(4-tert-Butylphenyl)-[1,3,4]oxadiazole-2-carboxylic acid, (1-phenylethyl)amide;
5-(4-Trifluoromethylphenyl)-[1,3,4]oxadiazole-2-carboxylic acid, (2-thienylmethyl)amide;
(S)-5-(4-Methoxyphenyl)-[1,3,4]oxadiazole-2-carboxylic acid, (1-phenylethyl)amide;
(S)-5-(2-Chlorophenyl)-[1,3,4]oxadiazole-2-carboxylic acid, (1-phenylethyl)amide;
(S)-5-(4-Trifluoromethylphenyl)-[1,3,4]oxadiazole-2-carboxylic acid, (1-phenylethyl)amide;
(S)-5-(2,6-Difluorophenyl)-[1,3,4]oxadiazole-2-carboxylic acid, (1-phenylethyl)amide;
(R/S)-5-(4-Fluorophenyl)-[1,3,4]oxadiazole-2-carboxylic acid, [1-(2-thienyl)ethyl]amide;
(R/S)-5-(2-Fluorophenyl)-[1,3,4]oxadiazole-2-carboxylic acid, [1-(2-thienyl)ethyl]amide;
(R/S)-5-(4-Chlorophenyl)-[1,3,4]oxadiazole-2-carboxylic acid, [1-(2-thienyl)ethyl]amide;
(S)-5-(2,4-Difluorophenyl)-[1,3,4]oxadiazole-2-carboxylic acid, (1-phenylethyl)amide;
(R/S)-5-(4-tertButylphenyl)-[1,3,4]oxadiazole-2-carboxylic acid, [1-(2-thienyl)ethyl]amide;
(R/S)-5-(4-Trifluoromethylphenyl)-[1,3,4]oxadiazole-2-carboxylic acid, [1-(2-thienyl)ethyl]amide;
(R/S)-5-(4-Methoxyphenyl)-[1,3,4]oxadiazole-2-carboxylic acid, [1-(2-thienyl)ethyl]amide;
(R/S)-5-(2,4-Difluorophenyl)-[1,3,4]oxadiazole-2-carboxylic acid, [1-(2-thienyl)ethyl]amide;
(R/S)-5-(2,6-Difluorophenyl)-[1,3,4]oxadiazole-2-carboxylic acid, [1-(2-thienyl)ethyl]amide;
(R/S)-5-Cyclopentyl-[1,3,4]oxadiazole-2-carboxylic acid, [1-(2-thienyl)ethyl]amide;
(S)-5-Cyclopentyl-[1,3,4]oxadiazole-2-carboxylic acid, (1-phenylethyl)amide;
5-tert-Butyl-[1,3,4]oxadiazole-2-carboxylic acid, (2-thienylmethyl)amide;
(S)-5-Phenyl-[1,3,4]oxadiazole-2-carboxylic acid, [1-(2-thienyl)ethyl]amide;
(S)-5-(4-Fluorophenyl)-[1,3,4]oxadiazole-2-carboxylic acid, [1-(2-thienyl)ethyl]amide;
(S)-5-(2-Fluorophenyl)-[1,3,4]oxadiazole-2-carboxylic acid, [1-(2-thienyl)ethyl]amide;
(S)-5-(4-Chlorophenyl)-[1,3,4]oxadiazole-2-carboxylic acid, [1-(2-thienyl)ethyl]amide;
(S)-5-(2,4-Difluorophenyl)-[1,3,4]oxadiazole-2-carboxylic acid, [1-(2-thienyl)ethyl]amide;
(S)-5-(2,6-Difluorophenyl)-[1,3,4]oxadiazole-2-carboxylic acid, [1-(2-thienyl)ethyl]amide;
(S)-5-isoPropyl-[1,3,4]oxadiazole-2-carboxylic acid, (1.-phenylethyl)amide;
(S)-5-isoButyl-[1,3,4]oxadiazole-2-carboxylic acid, (1-phenylethyl)amide;
(S)-5-tert-Butyl-[1,3,4]oxadiazole-2-carboxylic acid, [1-(2-thienyl)ethyl]amide;
(R/S)-5-isoPropyl-[1,3,4]oxadiazole-2-carboxylic acid, [1-(2-thienyl)ethyl]amide;
(R/S)-5-isoButyl-[1,3,4]oxadiazole-2-carboxylic acid, [1-(2-thienyl)ethyl]amide;
(R/S)-5-(4-Fluorophenyl)-[1,3,4]oxadiazole-2-carboxylic acid, [1-(3-thienyl)ethyl]amide;
(R/S)-5-(4-tert-Butylphenyl)-[1,3,4]oxadiazole-2-carboxylic acid, [1-(3-thienyl)ethyl]amide; and
(R/S)-5-Phenyl-[1,3,4]thiadiazole-2-carboxylic acid, [1-(2-thienyl)ethyl]amide;
(S)-5-tert-Butyl-[1,3,4]thiadiazole-2-carboxylic acid, [1-(2-thienyl)ethyl]amide;
(S)-5-Phenyl-[1,3,4]thiadiazole-2-carboxylic acid, (1-phenylethyl) amide;
(R/S)-5-tert-Butyl-[1,3,4]thiadiazole-2-carboxylic acid, [1-(2-thienyl)ethyl]amide;
(R/S)-5-(4-Fluorophenyl)-[1,3,4]thiadiazole-2-carboxylic acid, (1-phenylethyl) amide;
(S)-5-(2-Fluorophenyl)-[1,3,4]thiadiazole-2-carboxylic acid, (1-phenylethyl)amide;
(S)-5-(4-Chlorophenyl)-[1,3,4]thiadiazole-2-carboxylic acid, (1-phenylethyl)amide;
5-(4-tert-Butylphenyl)-[1,3,4]thiadiazole-2-carboxylic acid, (2-thienylmethyl)amide;
(S)-5-(4-tert-Butylphenyl)-[1,3,4]thiadiazole-2-carboxylic acid, (1-phenylethyl)amide;
5-(4-Trifluoromethylphenyl)-[1,3,4]thiadiazole-2-carboxylic acid, (2-thienylmethyl)amide;
(S)-5-(4-Methoxyphenyl)-[1,3,4]thiadiazole-2-carboxylic acid, (1-phenylethyl)amide;
(S)-5-(2-Chlorophenyl)-[1,3,4]thiadiazole-2-carboxylic acid, (1-phenylethyl)amide;
(S)-5-(4-Trifluoromethylphenyl)-[1,3,4]thiadiazole-2-carboxylic acid, (1-phenylethyl)amide;
(S)-5-(2,6-Difluorophenyl)-[1,3,4]thiadiazole-2-carboxylic acid, (1-phenylethyl)amide;
(R/S)-5-(4-Fluorophenyl)-[1,3,4]thiadiazole-2-carboxylic acid, [1-(2-thienyl)ethyl]amide;
(R/S)-5-(2-Fluorophenyl)-[1,3,4]thiadiazole-2-carboxylic acid, [1-(2-thienyl)ethyl]amide;
(R/S)-5-(4-Chlorophenyl)-[1,3,4]thiadiazole-2-carboxylic acid, [1-(2-thienyl)ethyl]amide;
(S)-5-(2,4-Difluorophenyl)-[1,3,4]thiadiazole-2-carboxylic acid, (1-phenylethyl)amide;
(R/S)-5-(4-tertButylphenyl)-[1,3,4]thiadiazole-2-carboxylic acid, [1-(2-thienyl)ethyl]amide;
(R/S)-5-(4-Trifluoromethylphenyl)-[1,3,4]thiadiazole-2-carboxylic acid, [1-(2-thienyl)ethyl]amide;
(R/S)-5-(4-Methoxyphenyl)-[1,3,4]thiadiazole-2-carboxylic acid, [1 -(2-thienyl)ethyl]amide;
(R/S)-5-(2,4-Difluorophenyl)-[1,3,4]thiadiazole-2-carboxylic acid, [1-(2-thienyl)ethyl]amide;
(R/S)-5-(2,6-Difluorophenyl)-[1,3,4]thiadiazole-2-carboxylic acid, [1-(2-thienyl)ethyl]amide;
(R/S)-5-Cyclopentyl-[1,3,4]thiadiazole-2-carboxylic acid, [1-(2-thienyl)ethyl]amide;
(S)-5-Cyclopentyl-[1,3,4]thiadiazole-2-carboxylic acid, (1-phenylethyl)amide;
5-tert-Butyl-[1,3,4]thiadiazole-2-carboxylic acid, (2-thienylmethyl)amide;
(S)-5-Phenyl-[1,3,4]thiadiazole-2-carboxylic acid, [1-(2-thienyl)ethyl]amide;
(S)-5-(4-Fluorophenyl)-[1,3,4]thiadiazole-2-carboxylic acid, [1-(2-thienyl)ethyl]amide;

(S)-5-(2-Fluorophenyl)-[1,3,4]thiadiazole-2-carboxylic acid, [1-(2-thienyl)ethyl]amide;
(S)-5-(4-Chlorophenyl)-[1,3,4]thiadiazole-2-carboxylic acid, [1-(2-thienyl)ethyl]amide;
(S)-5-(2,4-Difluorophenyl)-[1,3,4]thiadiazole-2-carboxylic acid, [1-(2-thienyl)ethyl]amide;
(S)-5-(2,6-Difluorophenyl)-[1,3,4]thiadiazole-2-carboxylic acid, [1-(2-thienyl)ethyl]amide;
(S)-5-isoPropyl-[1,3,4]thiadiazole-2-carboxylic acid, (1-phenylethyl)amide;
(S)-5-isoButyl-[1,3,4]thiadiazole-2-carboxylic acid, (1-phenylethyl)amide;
(S)-5-tert-Butyl-[1,3,4]thiadiazole-2-carboxylic acid, [1-(2-thienyl)ethyl]amide;
(R/S)-5-isoPropyl-[1,3,4]thiadiazole-2-carboxylic acid, [1-(2-thienyl)ethyl]amide;
(R/S)-5-isoButyl-[1,3,4]thiadiazole-2-carboxylic acid, [1-(2-thienyl)ethyl]amide;
(R/S)-5-(4-Fluorophenyl)-[1,3,4]thiadiazole-2-carboxylic acid, [1-(3-thienyl)ethyl]amide; and
(R/S)-5-(4-tert-Butylphenyl)-[1,3,4]thiadiazole-2-carboxylic acid, [1-(3-thienyl)ethyl]amide.

The invention also provides a process for the preparation of a compound of general formula I, which comprises reacting a compound of the general formula II

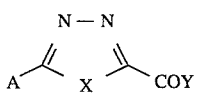 (II)

wherein A and X are as defined above for (I) and Y represents a leaving group, with a compound of general formula III

HNR¹R² (III)

wherein R¹ and R² are as defined above.

A suitable leaving Group Y is a halogen atom, especially chlorine; an acyloxy group, for example, acetoxy; an alkoxy group, suitably a methoxy or ethoxy group; or an aryloxy group, for example, a phenoxy group. Preferably, Y is a methoxy or ethoxy group.

In practice, the reaction may be carried out in the absence or presence of a solvent which promotes the reaction or at least does not interfere with it, for example toluene, xylene, ethanol, methanol, isopropanol. Mixtures of solvents may also be employed.

When Y is an alkoxy group, the reaction is suitably carried out in an organic solvent, for example ethanol or toluene, and in a temperature range from room temperature to the reflux temperature of the mixture. The reaction has been found to work most effectively when carried out under basic conditions. The basic conditions can suitably be provided by employing an excess of the amine III in the reaction, suitably a twofold excess of III with respect to II. Alternatively, the basic conditions can be provided by the separate inclusion of a base in the reaction mixture with II and III. The base may be any of those commonly employed in organic chemistry, for instance, a hydroxide, hydride, alkoxide, carbonate or hydrogen carbonate salt of a metal from Groups I or II of the Periodic Table; or an amine. A particularly suitable base is a tertiary amine, for example triethylamine.

In a variation of the above process, a compound of formula I is prepared by reacting a compound of formula II with a salt of general formula IV

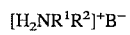 (IV)

wherein R¹ and R² are as defined hereinbefore and B⁻ is an anionic species, for example a chloride, bromide, iodide, sulphate or (R)-2-hydroxy-succinate, in the presence of a base. The reaction is typically carried out in an organic solvent, for example ethanol or toluene, and in a temperature range from room temperature to the reflux temperature of the mixture. The base may be any of those commonly employed in organic chemistry, for instance, a hydroxide, hydride, alkoxide, carbonate or hydrogen carbonate salt of a metal from Groups I or II of the Periodic Table; or an amine. A particularly suitable base is a tertiary amine, for example triethylamine, which may be present in a several-fold excess, for example four-fold.

Many starting [1,3,4]oxadiazole- and [1,3,4]thiadiazole-carboxylates II are known or may be prepared for example by known methods, such as those described by W. Ogilvie et al, *Can. J. Chem.*, 65, 166, (1987); D. Bartholomew et al, *Tetrahedron Lett.*, 2827, (1979); H. Hagen et al, *Liebigs Ann. Chem.*, 1216, (1980); and R. Boesch et al, Get. Often. DE 2808842.

A convenient procedure for the preparation of 5-aryl-[1,3,4]oxadiazole-2-carboxylates II (X=O, A=Ar, Y=alkoxy, aryloxy) has been found to be that which is reported by Huisgen et al, *Chem. Ber.*, 93, 2106, (1960) for the preparation of ethyl 5-phenyl-[1,3,4]oxadiazole-2-carboxylate from 5-phenyl-tetrazole and ethyl oxalyl chloride. Dahle (U.S. Pat. No. 3,790,588) discloses a similar method for the preparation of 5-aryl-[1,3,4]oxa- and -[1,3,4]thiadiazole alkylamines.

The present invention also provides an alternative process for the preparation of [1,3,4]-oxadiazole-carboxylates II (X=O, Y=alkoxy, aryloxy), which has been found to be particularly convenient and general. This comprises reacting a 1H-tetrazole-5-carboxylic acid derivative of general formula (V)

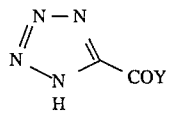 (V)

wherein Y is as defined hereinbefore, with a compound of general formula

A—COCl (VI)

wherein A is as defined hereinbefore. 1H-Tetrazole-5-carboxylic acid derivatives (V) are known or can be prepared, for example, as described by D. Moderhack, *Chem. Ber.*, 108, 887, (1975), and references therein. Compounds of formula (VI) are either known or can be obtained from known materials by standard techniques. The process is suitably carried out using approximately equimolar quantities of V and VI, suitably in the presence of an inert organic solvent, for example toluene, and in a temperature range from room temperature to the reflux temperature of the mixture.

The amines of formula III and the salts of formula IV are known or may be obtained from known materials by standard techniques.

The compounds of general formula I have been found to show interesting activity as herbicides. Accordingly, the invention further provides a herbicidal composition comprising a compound of formula I as defined above in association with at least one carrier, and a method of making such a composition which comprises bringing a compound of formula I into association with at least one carrier. Preferably there are at least two carriers, at least one of which is a surface-active agent.

The invention also provides a method of combating undesired plant growth at a locus, comprising application of an effective amount of such a compound or composition.

Particularly interesting activity has been found against grasses and broad leaf weeds, pre- and post-emergence. Selectivity in important crop species such as wheat, barley, maize, rice and soya-beans has also been found. This activity provides a further aspect of the present invention.

In a method as mentioned above, the dosage of the active ingredient, the compound of general formula I, may, for example, be from 0.01 to 10 kg/ha, suitably 0.05 to 4 kg/ha. The locus may be an agricultural or horticultural locus, comprising, for example, a plant or soil. In a preferred method the locus contains undesired plant growth and treatment is by foliar spray application.

A carrier in a composition according to the invention is any material with which the active ingredient is formulated to facilitate application to the locus to be treated, or to facilitate storage, transport or handling. A carrier may be a solid or a liquid, including a material which is normally gaseous but which has been compressed to form a liquid, and any of the carriers normally used in formulating pesticidal compositions may be used. Preferably compositions according to the invention contain 0.5 to 95% by weight of active ingredient.

Suitable solid carders include natural and synthetic days and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carders include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosene and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus, preferably at least one carrier in a composition according to the invention is a surface-active agent. For example the composition may contain at least two carders, at least one of which is a surface-active agent.

A surface-active agent may be an emulsifying agent, a dispersing agent or a wetting agent; it may be non-ionic or ionic. Examples of suitable surface-active agents include the sodium or calcium salts of polyacrylic acids and lignin sulphonic adds; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkaryl sulphonates such as dodecylbenzene sulphonate; and polymers of ethylene oxide and copolymers of ethylene oxide and propylene oxide.

The compositions of the new invention may for example be formulated as wettable powders, dusts, granules, solutions, emulsifiable concentrates, emulsions, suspension concentrates and aerosols. Wettable powders usually contain 25, 50 or 75% w/w of active ingredient and usually contain in addition to solid inert carrier, 3–10% w/w of a dispersing agent and, where necessary, 0–10% w/w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing 0.5–10% w/w of active ingredient. Granules are usually prepared to have a particle size between 10 and 100 BS mesh (1.676–0.152 mm), and may be manufactured by agglomeration or impregnation techniques. Generally, granules will contain 0.5–75% w/w active ingredient-and 0–10% w/w of additives such as stabilisers, surfactants, slow release modifiers and binding agents. The so-called 'dry flowable powders' consist of relatively small granules having a relatively higher concentration of active ingredient. Emulsiflable concentrates usually contain, in addition to a solvent and, when necessary, co-solvent, 10–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% WAN active ingredient, 0.5–15% w/w of dispersing agents, 0.1–10% w/w of suspending agents such as protective colloids and thixotropic agents, 0–10% w/w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise'-like consistency.

The composition of the invention may also contain other ingredients, for example other compounds possessing herbicidal, insecticidal or fungicidal properties.

The invention is illustrated by the following Examples.

EXAMPLE 1

(R/S)-5-Phenyl-[1,3,4]oxadiazole-2-carboxylic acid (1-thienyl)ethyl]amide (a) Ethyl 5-phenyl-[1,3,4]oxadiazole-2-carboxylate A suspension of 5-phenyltetrazole (6.58 g, 45 mmol) and ethyl oxalyl chloride (6.14 g, 45 mmol) in dry toluene (150 ml) is refluxed for 90 min. The solvent is evaporated in vacuo and the residue is purified by flash column chromatography (silica gel, hexane/ethyl acetate 4:1 v/v) to give ethyl 5-phenyl-[1,3,4]oxadiazole-2-carboxylate (8.8 g, 90%) as colourless crystals, m.p. 68°–70° C.

(b) (R/S)-5-Phenyl-[1,3,4]oxadiazole-2-carboxylic acid (1-thienyl)ethyl]amide

A solution of ethyl 5-phenyl-[1,3,4]oxadiazole-2-carboxylate (1.31 g, 6 mmol) and (R/S)-1-thienyl)ethylamine (1.53 g, 12 mmol) in absolute ethanol (20 ml) is refluxed for 2 days. The solvent is evaporated in vacuo and the residue is purified by flash column chromatography (silica gel, hexane/ethyl acetate 4:1 v/v) to give (R/S)-5-phenyl-[1,3,4] oxadiazole-2-carboxylic acid (1-thienyl)ethyl]amide (1.60 g, 89%) as colourless crystals, m.p. 155°–158° C.

EXAMPLE 2

(S)-5-tert-Butyl-[1,3,4]oxadiazole-2-carboxylic acid (1-phenylethyl)amide (a) Ethyl 5-tert-butyl-[1,3,4]oxadiazole-2-carboxylate A solution of ethyl tetrazole-5-carboxylate (8.53 g, 60 mmol) and pivaloyl chloride (7.23 g, 60 mmol) in dry toluene (240 ml) is refluxed for 16 hours. After the solution has cooled to room temperature, it is washed two times with 1 N sodium hydroxide solution (20 ml) and then once with water (20 ml). The organic phase is dried over magnesium sulphate and the solvent is evaporated in vacuo to give ethyl 5-tert-butyl-[1,3,4]oxadiazole-2-carboxylate as a red oil (6.96 g, 59%), which is used in the following stage without further purification.

(b) (S)-5-tert-Butyl-[1,3,4]oxadiazole-2-carboxylic acid (1-phenylethyl)amide

A solution of ethyl 5-tert-butyl-[1,3,4]oxadiazole-2-carboxylate (1.38 g, 7 mmol) and (S)-1-phenylethylamine (1.70 g, 14 mmol) in absolute ethanol (25 ml) is refluxed for 6 hours. The solvent is evaporated in vacuo and the residue is purified by flash column chromatography (silica gel, hexane/ethyl acetate 4:1 v/v) to give (S)-5-tert-butyl-[1,3,4]oxadiazole-2-carboxylic acid (1-phenylethyl)amide (1.76 g, 92%) as colourless crystals, m.p. 123°–125° C.

EXAMPLE 3

(S)-5-tert-Butyl-[1,3,4]oxadiazole-2-carboxylic acid, [1-(2-thienyl)ethyl]amide (a) (S), [1-(2-thienyl)ethyl]ammonium (R)-2-hydroxysuccinate (R/S)-[1-(2-thienyl)ethyl]amine (381.6 g, 3.0 mol) is added dropwise to a stirred solution of D-(+)-2-hydroxysuccinic acid (402.3 g, 3.0 mol) in water (800 ml) at room temperature. During the addition, the temperature of the solution rises to 55°–60° C. The solution is allowed to stand at room temperature for ca. 16 hours, during which time a crystalline precipitate is formed. The precipitate is filtered off. The optical purity of the salt is determined as follows: A small quantity of the salt (ca. 1.0 g) is treated with a 10% molar excess of sodium hydroxide in water (ca. 10 ml), and the aqueous solution is extracted with dichloromethane. The organic phase is then dried over magnesium sulphate and the solvent is evaporated in vacuo. The optical purity of the sample of free amine so generated is determined by NMR spectroscopy. The bulk of the salt is then recrystallised from water and the optical purity of the amine portion of the salt is redetermined by the same procedure. This process is repeated until a satisfactory optical purity is achieved. If the salt is allowed to recrystallise slowly, a ratio of 92:8 of the S-enantiomer to the R-enantiomer of the amine can be obtained after a single recrystallisation. Yield of (S)-[1-(2-thienyl)ethyl]amide (R)-2-hydroxysuccinate: 195.0 g, 50% of theory. M.p.>300° C.

(b) (S)-5-ted-Butyl-[1,3,4]oxadiazole-2-carboxylic acid [1-(2-thienyl)ethyl]amide Triethylamine (2.34 g, 23 mmol) is added to a stirred suspension of (S [1-(2-thienyl)ethyl]ammonium (R)-2-hydroxysuccinate in absolute ethanol (30 ml), and stirring is continued for 30 min, during which time a clear solution is formed. 5-tert-Butyl-[1,3,4]oxadiazole-2-carboxylate (Example 2(a), 1.38 g, 7 mmol) is added and the mixture is refluxed for 16 h. The solvent is evaporated in vacuo and the residue is purified by flash column chromatography (silica gel, hexane/ethyl acetate 4:1 v/v) to give (S)-5-tert-butyl-[1,3,4]oxadiazole-2-carboxylic acid, [1-(2-thienyl)ethyl] amide (1.54 g, 79%) as a pale yellow oil.

Further Examples of general formula I in which $R^2$ is a group —$CH(R^3)R^4$ are prepared according to the methods of Examples 1–3 and are listed in Table 1 below. The structures of all products are confirmed by NMR spectroscopy.

TABLE 1

$$A \overset{N-N}{\underset{X}{\diagup \diagdown}} CON(R^1)-CH(R^3)R^4$$

| Ex. No. | X | A | $R^1$ | $R^3$ | $R^4$ | Stereo- chem. | mp (°C.) |
|---|---|---|---|---|---|---|---|
| 4 | O | Phenyl | H | Me | Phenyl | (S) | 135–138 |
| 5 | O | tert-Butyl | H | Me | 2-Thienyl | (R/S) | oil |
| 6 | O | Dimethylamino | H | Me | Phenyl | (S) | 133–136 |
| 7 | O | 4-Fluorophenyl | H | Me | Phenyl | (S) | 115–116 |
| 8 | O | 4-Fluorophenyl | H | H | 2-Thienyl | — | 198–200 |
| 9 | O | 4-Fluoro phenyl | H | H | Phenyl | — | 190–192 |
| 10 | O | 2-Fluoro phenyl | H | Me | Phenyl | (S) | 103–105 |
| 11 | O | 2-Fluorophenyl | H | H | 2-Thienyl | — | 165–168 |
| 12 | O | 4-Chlorophenyl | H | Me | Phenyl | (S) | 107–108 |
| 13 | O | 4-Chlorophenyl | H | H | 2-Thienyl | — | 213–216 |
| 14 | O | 4-tert-Butylphenyl | H | H | 2-Thienyl | — | 136–138 |
| 15 | O | Styryl | H | H | 2-Thienyl | — | 202–205 |
| 16 | O | 4-tert-Butylphenyl | H | Me | Phenyl | (S) | oil |
| 17 | O | Styryl | H | Me | Phenyl | (S) | 148–150 |
| 18 | O | 4-Trifluoromethylphenyl | H | H | 2-Thienyl | — | 174 |

TABLE 1-continued $$A \underset{X}{\overset{N-N}{\underset{\parallel}{\bigwedge}}} CON(R^1)-CH(R^3)R^4$$

| Ex. No. | X | A | R¹ | R³ | R⁴ | Stereo-chem. | mp (°C.) |
|---|---|---|---|---|---|---|---|
| 19 | O | 4-Methoxyphenyl | H | Me | Phenyl | (S) | 137–138 |
| 20 | O | 4-Methoxyphenyl | H | H | 2-Thienyl | — | 189–190 |
| 21 | O | 2-Chlorophenyl | H | Me | Phenyl | (S) | 104–106 |
| 22 | O | 2-Chlorophenyl | H | H | 2-Thienyl | — | 172 |
| 23 | O | 4-Trifluoromethylphenyl | H | Me | Phenyl | (S) | 78–80 |
| 24 | O | 2,6-diFluorophenyl | H | Me | Phenyl | (S) | 113 |
| 25 | O | 2,6-diChlorophenyl | H | Me | Phenyl | (S) | 120–122 |
| 26 | O | 2,4-di Chlorophenyl | H | Me | Phenyl | (S) | 105 |
| 27 | O | 3,4-di Chlorophenyl | H | Me | Phenyl | (S) | 115–117 |
| 28 | O | 3,5-di Chlorophenyl | H | Me | Phenyl | (S) | 122 |
| 29 | O | 4-Fluorophenyl | H | Me | 2-Thienyl | (R/S) | 171 |
| 30 | O | 2-Fluorophenyl | H | Me | 2-Thienyl | (R/S) | 137 |
| 31 | O | 4-Chlorophenyl | H | Me | 2-Thienyl | (R/S) | 135 |
| 32 | O | 2,4-di Fluorophenyl | H | Me | Phenyl | (S) | 73 |
| 33 | O | 4-tert-Butylphenyl | H | Me | 2-Thienyl | (R/S) | 98 |
| 34 | O | Styryl | H | Me | 2-Thienyl | (R/S) | 140 |
| 35 | O | 4-Trifluoromethylphenyl | H | Me | 2-Thienyl | (R/S) | 120 |
| 36 | O | 4-Methoxyphenyl | H | Me | 2-Thienyl | (R/S) | 139 |
| 37 | O | 2,4-diFluorophenyl | H | Me | 2-Thienyl | (R/S) | 137 |
| 38 | O | 2,6-diFluorophenyl | H | Me | 2-Thienyl | (R/S) | 112 |
| 39 | O | 2,6-diChlorophenyl | H | Me | 2-Thienyl | (R/S) | 167 |
| 40 | O | 2,4-diChlorophenyl | H | Me | 2-Thienyl | (R/S) | 134 |
| 41 | O | 3,4-diChlorophenyl | H | Me | 2-Thienyl | (R/S) | 157 |
| 42 | O | Cyclopentyl | H | Me | 2-Thienyl | (R/S) | 82 |
| 43 | O | 3,5-di-Chlorophenyl | H | Me | 2-Thienyl | (R/S) | 154 |
| 44 | O | Cyclopentyl | H | Me | Phenyl | (S) | oil |
| 45 | O | tert-Butyl | H | H | 2-Thienyl | — | 75–78 |
| 46 | O | Cyclopentyl | H | H | 2-Thienyl | — | 80–83 |
| 47 | O | Phenyl | H | Me | 2-Thienyl | (S) | 132–135 |
| 48 | O | 4-Fluorophenyl | H | Me | 2-Thienyl | (S) | 139–142 |
| 49 | O | 2-Fluorophenyl | H | Me | 2-Thienyl | (S) | 119 |
| 50 | O | 4-Chlorophenyl | H | Me | 2-Thienyl | (S) | 117 |
| 51 | O | 2,4-diFluorophenyl | H | Me | 2-Thienyl | (S) | 108–110 |
| 52 | O | 2,6-diFluorophenyl | H | Me | 2-Thienyl | (S) | 128–129 |
| 53 | O | isoPropyl | H | Me | Phenyl | (S) | 61 |
| 54 | O | isoPropyl | H | H | 2-Thienyl | — | 70 |
| 55 | O | isoButyl | H | Me | Phenyl | (S) | 63 |
| 56 | O | isoButyl | H | H | 2-Thienyl | — | 79 |
| 57 | O | 4-tert-Butylphenyl | H | Me | 2-Thienyl | (S) | oil |
| 58 | O | isoPropyl | H | Me | 2-Thienyl | (R/S) | 58 |
| 59 | O | isoButyl | H | Me | 2-Thienyl | (R/S) | 69 |
| 60 | O | 4-Fluorophenyl | H | Me | 3-Thienyl | (R/S) | 143–145 |
| 61 | O | 4-tert-Butylphenyl | H | Me | 3-Thienyl | (R/S) | oil |

EXAMPLE 62

Herbicidal Activity

To evaluate their herbicidal activity, compounds according to the invention are tested using a representative range of plants:

| | |
|---|---|
| TRZAW | Triticum aestivum |
| HORVW | Hordeum vulgare |
| ZEAMX | Zea mays |
| GOSHI | Gossypium hirsutum |
| HELAN | Helianthus annuus |
| GLYMA | Glycine max |
| ALOMY | Alopecurus myosuroides |
| SETVI | Setaria viridis |
| ECHCG | Echinochloa crus-galli |
| GALAP | Galium aparine |
| STEME | Stellaria media |
| VERPE | Veronica persica |
| VIOAR | Viola arvensis |
| IPOHE | Ipomoea hederacea |
| LAMPU | Lamium purpureum |
| PAPRH | Papaver rhoeas |
| MATIN | Matricaria inodora |
| AMARE | Amaranthus retroflexus |
| ABUTH | Abutilon theophrasti |
| AMBEL | Ambrosia artemisifolia |
| CHEAL | Chenopodium album |

The tests fall into two categories, preemergence and postemergence. The preemergence tests involve spraying a liquid formulation of the compound onto the soil in which the seeds have recently been sown. The postemergence tests involve spraying a liquid formulation of the compound onto seedling plants.

The soil used in the tests is a prepared horticultural loam.

The formulations used in the tests are prepared from solutions of the test compounds in acetone containing 0.4% by weight of an alkylphenol/ethylene oxide condensate available under the trade mark TRITON X-155. These acetone solutions are diluted with water and the resulting formulations applied at dosage levels corresponding to 800 g of active material per hectare in a volume equivalent to 900 liters per hectare.

In the preemergence tests untreated sown soil and in the postemergence tests untreated soil bearing seedling plants are used as controls.

WEED CONTROL OBSERVATIONS (techniques and timing):

Results of herbicide evaluation are expressed on a rating scale (0–9). The scale is based upon a visual observation of plant stand, vigor, malformation, size, chlorosis, and general plant appearance as compared to a control. Preemergence and postemergence treatments are evaluated at 3 and 2 weeks after treatment, respectively.

| Control Rating | Definition | % Control |
|---|---|---|
| 9 | complete kill | 100 |
| 8 | approaching complete kill | 91–99 |
| 7 | good herbicidal effect | 80–90 |
| 6 | herbicidal effect | 65–79 |
| 5 | definite injury | 45–64 |
| 4 | injury | 30–44 |
| 3 | moderate effect | 16–29 |
| 2 | slight effect | 6–15 |
| 1 | trace effect | 1–5 |
| 0 | no effect | 0 |
| X | unable to read sample | — |

The results of the tests are set out in Table 2 below. An asterisk denotes that the specified plant species is not treated in the test.

TABLE 2

| Ex. No. | Appl. Time | TRZAW | HOVW | ZEASMX | GOEHLI | HLAXAN | GLMMA | AEMVY | STCI | EHLCAG | GLRMP | SVTEE | VEROR | VIOH | ILOMPE | LPMPRU | PAATIN | MAAMRE | AMBUTH | AABMELL | CHEAL |
|---|---|---|---|---|---|---|---|---|---|---|---|---|---|---|---|---|---|---|---|---|---|
| 1 | pre | 0 | 0 | 0 | 0 | 0 | 0 | 0 | 4 | 0 | 0 | * | 5 | 6 | 5 | 7 | * | * | 0 | 0 | 0 | * |
|   | post | 2 | 5 | 3 | 9 | 9 | 8 | 2 | 9 | 6 | 6 | 9 | 9 | 9 | 5 | 4 | * | * | 9 | 8 | 8 | * |
| 2 | pre | 0 | 0 | 0 | 0 | 0 | 0 | 2 | 5 | 0 | 0 | 5 | 8 | 5 | 0 | 0 | * | * | 5 | 4 | 3 | * |
|   | post | 3 | 1 | 1 | 4 | 4 | 3 | 0 | 4 | 3 | 4 | 6 | 7 | 5 | 5 | 2 | * | * | 6 | 6 | 5 | * |
| 4 | pre | 0 | 0 | 1 | 0 | 0 | 0 | 0 | 4 | 4 | 0 | 6 | 6 | 6 | 0 | 3 | * | * | 8 | 1 | 0 | * |
|   | post | 4 | 5 | 3 | 9 | 9 | 8 | 4 | 8 | 5 | 8 | 9 | 9 | 7 | 9 | 6 | * | * | 9 | 9 | 9 | * |
| 5 | pre | 0 | 0 | 0 | 0 | 0 | 0 | 4 | 8 | 6 | 0 | 8 | 8 | 6 | 0 | 2 | * | * | 5 | 7 | 1 | * |
|   | post | 4 | 4 | 4 | 9 | 8 | 8 | 3 | 6 | 4 | 5 | 8 | 9 | 7 | 6 | 1 | * | * | 5 | 8 | 9 | * |
| 6 | pre | 0 | 0 | 0 | 0 | 0 | 0 | 0 | 0 | * | 0 | * | 0 | 2 | 0 | 0 | 0 | 0 | * | 0 | * | * |
| post | 1 | 2 | 0 | 2 | 2 | 0 | 2 | 0 | * | 2 | * | 0 | 0 | 2 | 1 | 0 | 0 | * | 2 | * | * | |
| 7 | pre | 0 | 0 | 0 | 0 | * | 1 | 4 | 9 | * | 1 | 9 | 9 | * | 0 | 9 | 9 | 9 | 9 | 8 | 0 | 8 |
|   | post | 4 | 5 | 2 | 9 | * | 8 | 5 | 9 | * | 7 | 9 | 9 | * | 9 | 9 | 9 | 9 | 9 | 9 | 8 | 9 |
| 8 | pre | 0 | 0 | 2 | 2 | * | 2 | 0 | 3 | * | 0 | 7 | 7 | * | 0 | 0 | 9 | 5 | 9 | 0 | 3 | 5 |
|   | post | 0 | 0 | 0 | 0 | * | 0 | 0 | 0 | * | 0 | 5 | 4 | * | 0 | 0 | 3 | 2 | 8 | 3 | 3 | 4 |
| 9 | pre | 0 | 0 | 0 | 0 | * | 1 | 0 | 3 | * | 0 | 0 | 7 | * | 0 | 0 | 6 | 0 | 0 | 0 | 0 | 0 |
|   | post | 0 | 0 | 0 | 0 | * | 0 | 0 | 0 | * | 0 | 0 | 0 | * | 0 | 0 | 0 | 0 | 0 | 3 | 0 | 0 |
| 10 | pre | 0 | 0 | 0 | 0 | * | 2 | 1 | 3 | * | 0 | 9 | 9 | * | 0 | 8 | 9 | 8 | 8 | 0 | 3 | 8 |
|    | post | 2 | 4 | 3 | 8 | * | 4 | 0 | 9 | * | 6 | 9 | 9 | * | 8 | 8 | 8 | 0 | 9 | 9 | 7 | 7 |
| 11 | pre | 0 | 0 | 1 | 0 | * | 0 | 0 | 3 | * | 0 | 7 | 7 | * | 0 | 0 | 8 | 2 | 7 | 0 | 0 | 3 |
|    | post | 0 | 0 | 0 | 1 | * | 0 | 0 | 0 | * | 0 | 7 | 6 | * | 0 | 0 | 7 | 0 | 9 | 5 | 4 | 8 |
| 12 | pre | 0 | 0 | 0 | 0 | * | 0 | 1 | 9 | * | 0 | 9 | 9 | * | 0 | 8 | 9 | 7 | 8 | 2 | 0 | 8 |
|    | post | 2 | 4 | 3 | 9 | * | 5 | 3 | 9 | * | 6 | 9 | 9 | * | 9 | 9 | 9 | 5 | 9 | 9 | 7 | 9 |
| 16 | pre | 0 | 0 | 0 | 0 | * | 0 | 0 | 8 | * | 0 | 6 | 9 | * | 1 | 8 | 9 | 9 | 9 | 1 | 3 | 7 |
|    | post | 2 | 4 | 3 | 9 | * | 4 | 3 | 9 | * | 7 | 9 | 9 | * | 8 | 9 | 7 | 9 | 9 | 8 | 8 | 7 |
| 17 | pre | 0 | 0 | 1 | 3 | * | 0 | 0 | 0 | * | 0 | 0 | 3 | * | 0 | 0 | 5 | 0 | 0 | 0 | 0 | 0 |
|    | post | 0 | 0 | 1 | 3 | * | 0 | 0 | 0 | * | 2 | 0 | 3 | * | 1 | 6 | 5 | 0 | 4 | 1 | 0 | 5 |
| 19 | pre | 0 | 0 | 0 | 0 | * | 0 | 0 | 7 | * | 0 | 6 | 9 | * | 0 | 8 | 9 | 7 | 9 | 1 | 0 | 9 |
|    | post | 2 | 3 | 3 | 9 | * | 4 | 3 | 9 | * | 5 | 8 | 9 | * | 6 | 8 | 7 | 6 | 8 | 9 | 7 | 8 |
| 21 | pre | 0 | 0 | 0 | 0 | * | 0 | 0 | 1 | * | 0 | 5 | 9 | * | 1 | 5 | 9 | 6 | 3 | 0 | 0 | 2 |
|    | post | 2 | 1 | 2 | 8 | * | 2 | 0 | 6 | * | 4 | 9 | 7 | * | 4 | 6 | 5 | 4 | 8 | 5 | 6 | 7 |
| 23 | pre | 0 | 0 | 0 | 1 | 0 | * | 0 | 4 | 8 | * | 0 | 8 | 9 | * | 0 | 7 | 9 | 8 | 9 | 5 | 0 | 8 |
|    | post | 3 | 4 | 3 | 9 | * | 5 | 3 | 9 | * | 7 | 9 | 9 | * | 8 | 9 | 8 | 8 | 9 | 9 | 8 | 9 |
| 24 | pre | 0 | 0 | 0 | 0 | * | 0 | 2 | 8 | * | 0 | 8 | 9 | * | 2 | 7 | 9 | 9 | 9 | 7 | 3 | 8 |
|    | post | 3 | 2 | 2 | 8 | * | 4 | 2 | 6 | * | 5 | 8 | 9 | * | 5 | 8 | 6 | 4 | 9 | 9 | 8 | 9 |
| 25 | pre | 0 | 0 | 0 | 0 | * | 0 | 0 | 0 | * | 0 | 0 | 0 | * | 0 | 0 | 3 | 0 | 3 | 0 | 0 | 0 |
|    | post | 0 | 0 | 0 | 0 | * | 1 | 0 | 0 | * | 0 | 0 | 0 | * | 1 | 1 | 2 | 0 | 5 | 1 | 0 | 5 |
| 26 | pre | 0 | 0 | 0 | 0 | * | 0 | 0 | 0 | * | 0 | 0 | 7 | * | 0 | 0 | 9 | 0 | 3 | 0 | 0 | 0 |
|    | post | 0 | 0 | 0 | 3 | * | 2 | 0 | 4 | * | 0 | 6 | 3 | * | 0 | 7 | 3 | 2 | 8 | 1 | 0 | 5 |
| 27 | pre | 0 | 0 | 0 | 0 | * | 0 | 0 | 0 | * | 0 | 0 | 3 | * | 0 | 0 | 3 | 0 | 0 | 0 | 0 | 0 |
|    | post | 0 | 0 | 0 | 2 | * | 2 | 0 | 0 | * | 0 | 0 | 0 | * | 0 | 4 | 2 | 0 | 5 | 0 | 0 | 6 |
| 28 | pre | 0 | 0 | 0 | 0 | * | 0 | 0 | 0 | * | 0 | 0 | 0 | * | 0 | 0 | 0 | 0 | 0 | 0 | 0 | 0 |
|    | post | 0 | 0 | 0 | 0 | * | 2 | 0 | 0 | * | 0 | 0 | 0 | * | 0 | 0 | 0 | 0 | 0 | 0 | 0 | 2 |
| 32 | pre | 0 | 0 | 0 | 0 | * | 0 | 3 | 9 | * | 2 | 9 | 9 | * | 0 | 8 | 8 | 9 | 9 | 2 | 1 | 8 |
|    | post | 3 | 3 | 3 | 9 | * | 5 | 3 | 9 | * | 6 | 9 | 9 | * | 9 | 9 | 9 | 9 | 8 | 8 | 8 | 9 |

I claim:
1. A compound of formula I

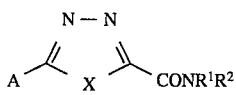

wherein

X represents an oxygen or sulphur atom;

A represents an optionally substituted $C_{1-10}$ alkyl, optionally substituted $C_{2-8}$ alkenyl, optionally substituted $C_{3-8}$ cycloalkyl, optionally substituted $C_{3-8}$ cycloalkenyl, optionally substituted di($C_{1-6}$ alkyl)amino, optionally substituted phenyl, optionally substituted pyridyl, optionally substituted furyl, or optionally substituted thienyl;

$R^1$ represents hydrogen, an optionally substituted $C_{1-10}$ alkyl, or an optionally substituted $C_{2-8}$ acyl group;

$R^2$ represents a group —CH($R^3$)$R^4$;

$R_3$ represents hydrogen, methyl, or ethyl;

$R^4$ represents an optionally substituted phenyl group, an optionally substituted pyridyl, an optionally substituted furyl, an optionally substituted thiophenyl, or an optionally substituted benzothiophene;

said optionally substituted alkyl, alkenyl, cycloalkyl or cycloalkenyl moieties being unsubstituted or substituted with one to three halogen, phenyl, nitro, cyano, hydroxyl, $C_{1-4}$ alkoxy, $C_{1-4}$ alkyl, $C_{1-4}$ haloalkoxy, ($C_{1-4}$ alkoxy)carbonyl, amino, $C_{1-4}$ alkylsulphinyl, $C_{1-4}$ alkylsulphenyl, $C_{1-4}$ alkylsulphonyl, phenylsulphinyl, phenylsulphenyl, phenylsulphonyl, mono-($C_{1-4}$ alkyl)amino, or di-($C_{1-4}$ alkyl)amino groups;

said optionally substituted phenyl, pyridyl, furyl, thienyl, thiophenyl, or benzothiophene moieties being unsubstituted or substituted with one to five halogen, nitro, cyano, amino, hydroxyl, $C_{1-4}$ alkyl, $C_{1-4}$ haloalkyl, $C_{1-4}$ alkoxy, or $C_{1-4}$ haloalkoxy.

2. A compound as claimed in claim 1, wherein

A represents an optionally substituted alkyl, cycloalkyl, alkenyl, dialkylamino, phenyl, pyridyl, furyl or thienyl group.

3. A compound as claimed in claim 2, wherein

A represents a branched $C_{3-6}$ alkyl group, a cyclopentyl group, a styryl group, a dimethylamino group, or a phenyl group which is unsubstituted, or substituted by one or two moieties independently selected from halogen atoms, $C_{1-4}$ alkyl groups, $C_{1-4}$ alkoxy groups and $C_{1-4}$ haloalkyl groups.

4. A compound as claimed in claim 1, wherein

X represents an oxygen atom.

5. A compound as claimed in claim 1, wherein $R^3$ represents a hydrogen atom or a methyl group and $R^4$ represents an unsubstituted phenyl group or thienyl group.

6. A compound as claimed in claim 1, wherein the compound is an (S) isomer and the $R^2$ carbon atom being the point of attachment is optically active.

7. A herbicidal composition comprising at least one carrier and a compound of formula I, as defined in claim 1.

8. A composition as claimed in claim 7, comprising at least two carriers, at least one of which i a surface-active agent.

9. A method of combating undesired plant growth at a locus, comprising application to the locus of a compound of formula I, as defined in claim 1 or a composition as defined in claim 1.

* * * * *